(12) United States Patent
Yagi

(10) Patent No.: US 8,235,220 B2
(45) Date of Patent: Aug. 7, 2012

(54) SEPARATOR AND SEPARATOR CARTRIDGE

(75) Inventor: Hiroshi Yagi, Kamiina (JP)

(73) Assignee: Seiko Epson Corporation (JP)

( * ) Notice: Subject to any disclaimer, the term of this patent is extended or adjusted under 35 U.S.C. 154(b) by 148 days.

(21) Appl. No.: 12/879,445

(22) Filed: Sep. 10, 2010

(65) Prior Publication Data
US 2011/0079552 A1 Apr. 7, 2011

(30) Foreign Application Priority Data
Oct. 1, 2009 (JP) .................. 2009-229375

(51) Int. Cl.
*B01D 29/00* (2006.01)
(52) U.S. Cl. ............. 210/348; 210/433.1; 210/456; 210/498; 210/502.1; 210/506
(58) Field of Classification Search .......... 210/348, 210/433.1, 456, 498, 502.1, 506
See application file for complete search history.

(56) References Cited

U.S. PATENT DOCUMENTS
6,262,331 B1 * 7/2001 Nakahata et al. ........... 604/383

OTHER PUBLICATIONS

Sunitha Nagrath et al., "Isolation of Rare Circulating Tumour Cells in Cancer Patients by Microchip Technology", vol. 450\20/27, doi:10.1038, Nature 06385 Letters (Dec. 2007).

* cited by examiner

*Primary Examiner* — John Kim
(74) *Attorney, Agent, or Firm* — Harness, Dickey & Pierce, P.L.C.

(57) ABSTRACT

A separator includes: a channel having a first surface; a plurality of columnar members formed on the first surface and having a cross section in the shape of a crescent, the plurality of columnar members being arranged in a row direction along a longitudinal direction of the channel, and in a column direction perpendicular to the longitudinal direction of the channel, the columnar members that belong to the same row from among the plurality of columnar members being disposed so that the crescents face the same direction in the column direction, the columnar members that belong to a single row being disposed so that the crescents face the opposite direction in the column direction with respect to the crescents of the columnar members that belong to the adjacent row; and a substance that specifically binds to a separation target, and is disposed on side surfaces of the plurality of columnar members.

7 Claims, 9 Drawing Sheets

SEPARATOR AND SEPARATOR CARTRIDGE

CROSS-REFERENCE

This application claims priority to Japanese Patent Application No. 2009-229375, filed Oct. 1, 2009, the entirety of which is hereby incorporated by reference.

BACKGROUND

1. Technical Field

The present invention relates to separators, separator cartridges, and separator systems.

2. Related Art

Methods of chemical analysis, chemical synthesis, and other procedures including various analyses in bio-related fields using a microfluidic chip that includes microchannels in a glass substrate or the like have gained attention. The microfluidic chip, also known as a micro total analytical system (micro TAS) or a lab-on-a-chip, has advantages such as smaller amounts of samples and reagents, shorter reaction time, and less waste over common devices. Because of these advantages, the microfluidic chip is expected to have a wide range of applications, including medical diagnoses, on-site analyses of environment and food, and production of drugs and chemicals. Because the microfluidic chip requires only small amounts of reagent, the cost of tests can be reduced. Requiring small amounts of samples and reagents means a greatly shorter reaction time and improved test efficiency. Because specimens such as a sample blood are used in small amounts, the use of the microfluidic chip for medical diagnoses is particularly advantageous in terms of reducing the burden on patients.

Sunitha Nagrath et al., Isolation of rare circulating tumour cells in cancer patients by microchip technology, vol. 450|20/27, December 2007| doi:10.1038/nature06385 LETTERS describes a microchannel device that includes a plurality of cylindrical microposts disposed at regular intervals. In the microchannel device, an adherent factor is immobilized on the side surfaces of the cylindrical microposts, and the cancer cells in the blood flown in the microchannel device are removed by the adhesion of the adherent factor immobilized on the side surfaces of the cylindrical microposts. However, in the microchannel device, the ability of the adherent factor to adhere to the cancer cells is highly dependent on the flow rate of the blood, and the size and intervals of the cylindrical microposts. For example, when the blood flow rate is low, the cancer cells have less opportunity to contact the adherent factor, and only small numbers of cancer cells may be allowed to adhere to the cylindrical microposts. When the blood flow rate is high, there are cases where the cancer cells adhered to the cylindrical microposts are washed away. The cancer cells have only small opportunity to contact the adherent factor when the intervals between the cylindrical microposts are too large, and only small numbers of cancer cells may be allowed to adhere to the cylindrical microposts. Excessively small intervals between the cylindrical microposts increase the resistance against the blood flow, and the channels may be clogged by the adhered cancer cells.

SUMMARY

An advantage of some aspects of the present invention is to provide a separator, a separator cartridge, and a separator system with which the separation target can be efficiently separated from a separation target liquid.

According to a first aspect of the present invention, there is provided a separator that includes:

a channel having a first surface;

a plurality of columnar members formed on the first surface and having a cross section in the shape of a crescent, the plurality of columnar members being arranged in a row direction along a longitudinal direction of the channel, and in a column direction perpendicular to the longitudinal direction of the channel, the columnar members that belong to the same row from among the plurality of columnar members being disposed so that the crescents face the same direction in the column direction, the columnar members that belong to a single row being disposed so that the crescents face the opposite direction in the column direction with respect to the crescents of the columnar members that belong to the adjacent row; and a substance that specifically binds to a separation target, and is disposed on side surfaces of the plurality of columnar members.

As used herein, the term "crescent" means the shape that includes a first curve and a second curve, and in which the first curve and the second curve have maxima (minima) pointing the same direction. The shape of the crescent is such that, for example, one end portion of the first curve and one end portion of the second curve are in contact with each other, and that the other end portion of the first curve and the other end portion of the second curve are in contact with each other, or one end portion of the first curve and one end portion of the second curve are connected to each other via a curve or a straight line, and that the other end portion of the first curve and the other end portion of the second curve are connected to each other via a curve or a straight line. The first curve and the second curve require different curvatures when one end portion of the first curve and one end portion of the second curve are in contact with each other, and when the other end portion of the first curve and the other end portion of the second curve are in contact with each other.

In this case, the separator may be adapted so that the crescent includes a first curve, and a second curve having a greater curvature than the first curve, the first curve having an end portion in contact with one end portion of the second curve at a first end portion, the other end portion of the first curve being in contact with the other end portion of the second curve at a second end portion, and that a straight line $L_3$ lies between a straight line $L_1$ and a straight line $L_2$ under the conditions that:

$A_2$ is the second end portion of a columnar member A, $B_2$ is the second end portion of a columnar member B adjacent to the columnar member A in the column direction, $L_1$ is a straight line that extends from the second end portion $A_2$ of the columnar member A along a direction of a tangent line to the first curve at the second end portion $A_2$, $L_2$ is a straight line that extends from the second end portion $B_2$ of the columnar member B along a direction of a tangent line to the first curve at the second end portion $B_2$, M is the center of a segment that links the second end portion $A_2$ and the second end portion $B_2$, $C_1$ is the first end portion of a columnar member C adjacent to the columnar member A and the columnar members B in the row direction, and closest to the center M aside from the columnar member A and the columnar member B, and $L_3$ is a straight line that passes the first end portion $C_1$, and is parallel to the straight line $L_1$ and the straight line $L_2$.

In this case, a distance $w_1$ between the straight line $L_1$ and the straight line $L_3$, and a distance $w_2$ between the straight line $L_2$ and the straight line $L_3$ may be related to each other at the ratio $w_1/w_2$ of 0.8 to 1.2.

The separator includes a plurality of columnar members having a cross section in the shape of a crescent. The plurality of columnar members is arranged in a row direction along the longitudinal direction of the channel, and in a column direction perpendicular to the longitudinal direction of the channel. The columnar members that belong to the same row from among the plurality of columnar members are disposed so that the crescents face the same direction in the column direction. The columnar members that belong to a single row are disposed so that the crescents face the opposite direction in the column direction with respect to the crescents of the columnar members that belong to the adjacent row. Because a substance that specifically binds to the separation target is disposed on side surfaces of the plurality of columnar members, the separation target can be separated by allowing it to efficiently adhere to the side surfaces of the columnar members under the centripetal force that acts on the separation target.

According to a second aspect of the present invention, there is provided a separator cartridge that includes the separator.

According to a third aspect of the present invention, there is provided a separator system that includes the separator cartridge.

According to a fourth aspect of the present invention, there is provided a separator for separating a separation target from a separation target liquid, and that includes a channel through which the separation target liquid is flown, wherein the channel includes:

a first columnar member having a cross section in the shape of a crescent, and side surfaces on which a substance that specifically binds to the separation target is disposed;

a second columnar member having a cross section in the shape of a crescent, and that belongs to the same position as the first columnar member with respect to a first direction along a longitudinal direction of the channel, and to a position adjacent to the first columnar member with respect to a second direction orthogonal to the first direction, wherein the crescent of the second columnar member faces the same direction as the crescent of the first columnar member in the second direction, and wherein the substance is disposed on side surfaces of the second columnar member; and a third columnar member having a cross section in the shape of a crescent, and that belongs to a position adjacent to the first columnar member with respect to the first direction, wherein the crescent of the third columnar member faces the opposite direction in the second direction with respect to the crescent of the first columnar member, and wherein the substance is disposed on side surfaces of the third columnar member.

In this case, the separator is such that the crescent includes a first curve, and a second curve having a greater curvature than the first curve, the first curve having an end portion in contact with one end portion of the second curve at a first end portion, the other end portion of the first curve being in contact with the other end portion of the second curve at a second end portion, and that a straight line $L_3$ lies between a straight line $L_1$ and a straight line $L_2$ under the conditions that:

$A_2$ is the second end portion of the first columnar member, $B_2$ is the second end portion of the second columnar member, $L_1$ is a straight line that extends from the second end portion $A_2$ along a direction of a tangent line to the first curve of the first columnar member at the second end portion $A_2$, $L_2$ is a straight line that extends from the second end portion $B_2$ along a direction of a tangent line to the first curve of the second columnar member at the second end portion $B_2$, M is the center of a segment that links the second end portion $A_2$ and the second end portion $B_2$, $C_1$ is the first end portion of the third columnar member, and $L_3$ is a straight line that passes the first end portion $C_1$, and is parallel to the straight line $L_1$ and the straight line $L_2$.

In this case, a distance $w_1$ between the straight line $L_1$ and the straight line $L_3$, and a distance $w_2$ between the straight line $L_2$ and the straight line $L_3$ may be related to each other at the ratio $w_1/w_2$ of 0.8 to 1.2.

Because the straight line $L_3$ lies between the straight line $L_1$ and the straight line $L_2$, the separator can separate the separation target by allowing it to efficiently adhere to the side surfaces of the columnar members under the centripetal force that acts on the separation target.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following specifically describes a separator, a separator cartridge, and a separator system according to embodiments of the present invention.

1. First Embodiment

1.1. Configuration of Separator

Figure 1:
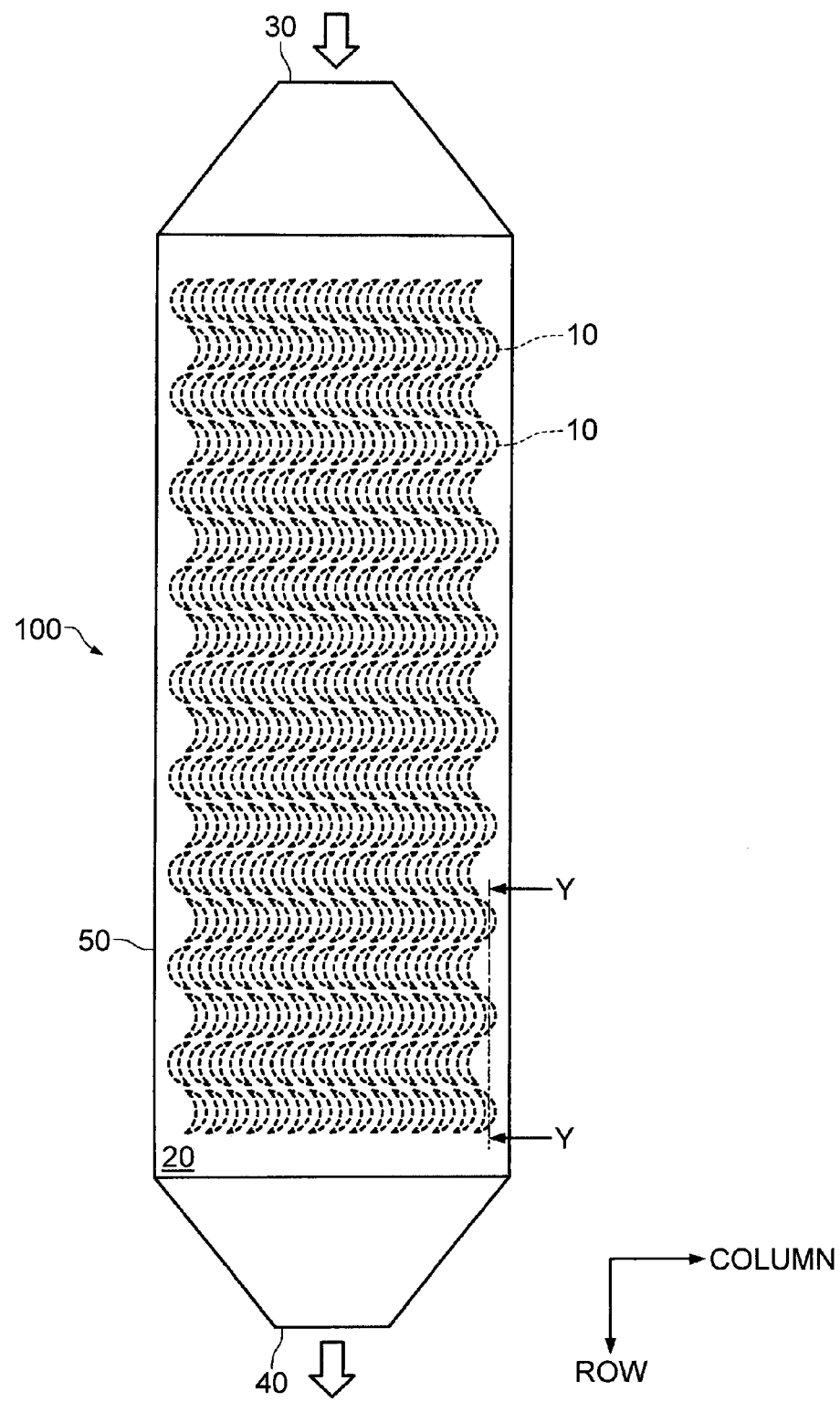
FIG. 1 is a plan view schematically illustrating a separator according to First Embodiment of the present invention.
Figure 2:
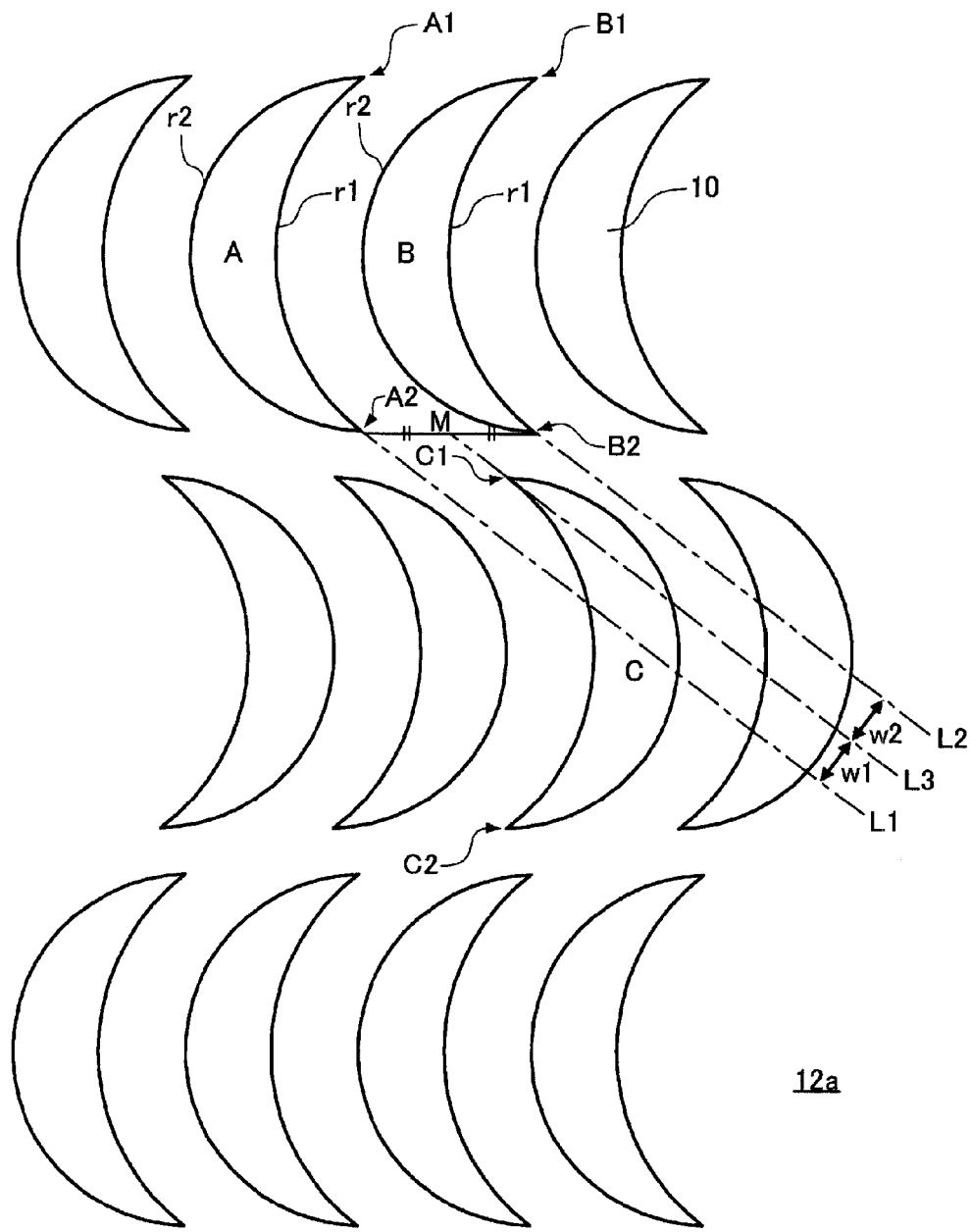
FIG. 2 is an enlarged view schematically illustrating a plane pattern of a plurality of columnar members provided in the channels shown in FIG. 1.
Figure 3:
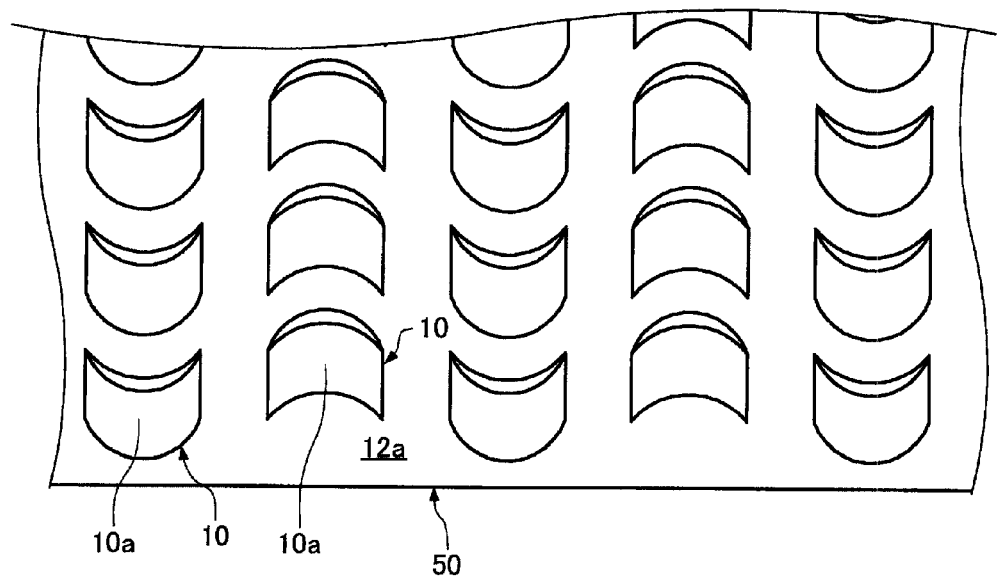
FIG. 3 is a perspective view schematically illustrating the columnar members provided in the channels shown in FIG. 1.
Figure 4:
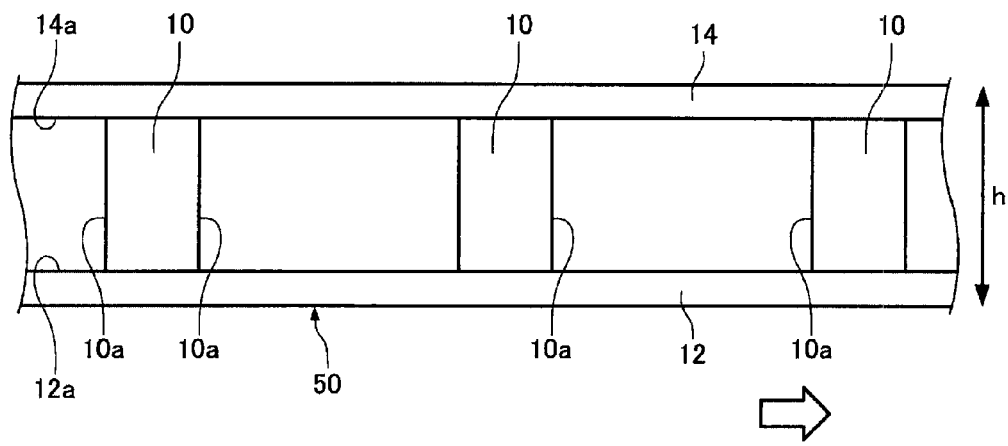
FIG. 4 is a cross sectional view showing a schematic illustration of the channels shown in FIG. 1.
Figure 5:
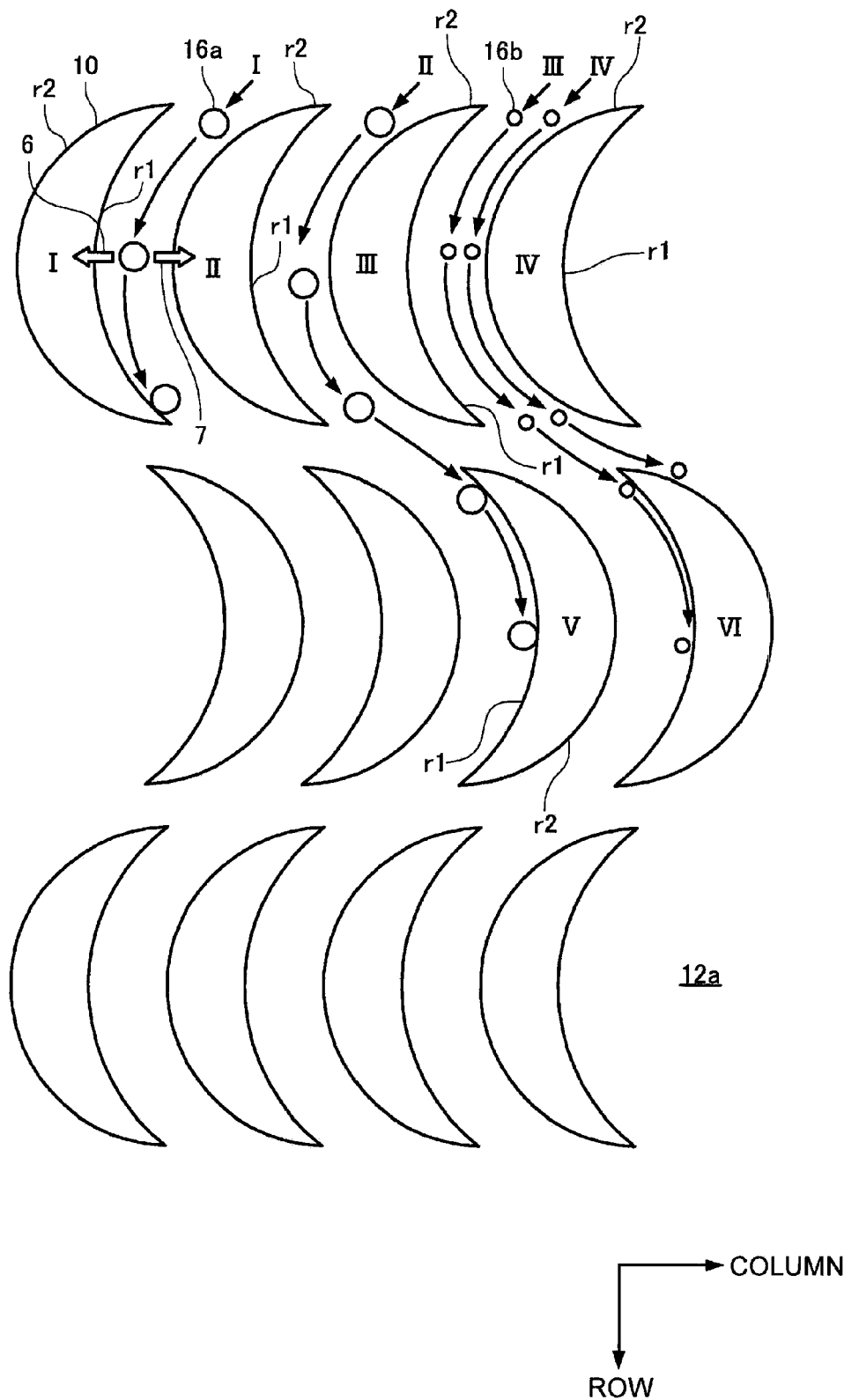
FIG. 5 is an explanatory diagram representing a method for separating a separation target using the channels shown in FIG. 1.

FIG. 1 is a plan view schematically illustrating a separator 100 according to an embodiment of the present invention. FIG. 2 is an enlarged view schematically illustrating a plane pattern of a plurality of columnar members 10 provided for channels 50 shown in FIG. 1. FIG. 3 is a perspective view schematically illustrating the columnar members 10 provided for the channels 50 shown in FIG. 1. FIG. 4 is a cross sectional view schematically illustrating the channels 50 shown in FIG. 1 (a cross section at Y-Y perpendicular to the plane of the paper). FIG. 5 is a diagram representing a method for separating a separation target using the channels 50 shown in FIG. 1.

As illustrated in FIG. 1, the separator 100 according to the embodiment of the invention includes the channels 50 provided with an inlet 30 and an outlet 40. A separation target liquid with a potential separation target is introduced through the inlet 30, and discharges through the outlet 40 after passing through the channels 50.

As illustrated in FIG. 4, the channels 50 include a first substrate (channel lower substrate) 12, a second substrate (channel upper substrate) 14, and a plurality of columnar members 10. Further, as illustrated in FIG. 4, the channels 50 includes a first surface 12a—the inner surface of the first substrate 12, and a second surface 14a—the inner surface of the second substrate 14 opposite the first surface 12a.

As illustrated in FIG. 1 to FIG. 3, the columnar members 10 have a cross section in the shape of a crescent. As illustrated in FIG. 4, the columnar members 10 are provided on the first surface 12a of the first substrate 12, and disposed between the first substrate 12 and the second substrate 14. Specifically, the columnar members 10 have upper surfaces in contact with the second surface 14a of the channels 50, and lower surfaces in contact with the first surface 12a of the channels 50. FIG. 3 illustrates the channels 50 without the second substrate 14.

In FIG. 1 to FIG. 3, the columnar members 10 are arranged in rows and columns, where the rows are directions along the longitudinal direction of the channels 50 (the flow direction of the separation target liquid), and the columns are directions perpendicular to the longitudinal direction of the channels 50. The columnar members 10 that belong to the same row are disposed at regular intervals. Further, the columnar members 10 that belong to the same row are disposed so that the crescents face the same direction in the column direction. Further, the columnar members 10 that belong to a single row are disposed so that the crescents face the opposite direction in the column direction with respect to the crescents of the columnar members that belong to the adjacent row. In other words, the crescents of the columnar members 10 of the adjacent columns (i.e., the columnar members 10 of a single row and the columnar members 10 of the adjacent row) are symmetrical about the row direction.

A substance that specifically binds to a separation target is disposed on side surfaces 10a of the columnar members 10. The separation target can be removed from the separation target liquid as it adheres to the side surfaces 10a of the columnar members 10. The substance that specifically binds to the separation target can be appropriately selected according to the properties and characteristics of the separation target.

As illustrated in FIG. 2, each crescent of the columnar members 10 has a first curve $r_1$ and a second curve $r_2$, and the second curve $r_2$ has a greater curvature than the first curve $r_1$. The crescent on the cross section of each columnar member 10 has a first end portion and a second end portion. Specifically, one of the end portions of the first curve $r_1$ and one of the end portions of the second curve $r_2$ are in contact with each other at the first end portion, and the other end portion of the first curve $r_1$ and the other end portion of the second curve $r_2$ are in contact with each other at the second end portion.

In FIG. 2, $A_2$ is the second end portion of a columnar member A, $B_2$ is the second end portion of a columnar member B adjacent to the columnar member A in the column direction, $L_1$ is the straight line that extends from the second end portion $A_2$ of the columnar member A along the direction of a tangent line to the first curve at the second end portion $A_2$, $L_2$ is the straight line that extends from the second end portion $B_2$ of the columnar member B along the direction of a tangent line to the first curve at the second end portion $B_2$, M is the center of the segment that links the second end portion $A_2$ and the second end portion $B_2$, $C_1$ is the first end portion of a columnar member C adjacent to the columnar member A and the columnar member B in the row direction, and closest to the center M aside from the columnar member A and the columnar member B, and $L_3$ is the straight line that passes the first end portion $C_1$, and is parallel to the straight line $L_1$ and the straight line $L_2$. The straight line $L_3$ lies between the straight line $L_1$ and the straight line $L_2$. In this way, the separation target that did not adhere to the side surfaces of the columnar member A has the chance to adhere to the side surfaces of the columnar member C adjacent to the columnar member A in the row direction, as will be described later.

Here, it is preferable that the distance $w_1$ between the straight line $L_1$ and the straight line $L_3$, and the distance w2 between the straight line $L_2$ and the straight line $L_3$ be related to each other at the ratio $w_1/w_2$ of 0.8 to 1.2. In this way, the separation target that has passed through between the columnar member A and the columnar member B has the greater chance to adhere to the side surfaces of the columnar member C. In the separator 100 of FIG. 1, $w_1/w_2=1.0$.

In the separator 100 according to the present embodiment, the first substrate 12, the second substrate 14, and the columnar members 10 may be made of any material, as long as it is not damaging to the components of the separation target liquid. For example, inorganic materials (including, for example, monocrystalline silicon and Pyrex® glass), and organic materials (for example, resin) can be used. For example, when the columnar members 10 are made of inorganic material, the dimensional accuracy of the columnar members 10 can be controlled with high accuracy by dry etching using photolithography. When resin is used, the columnar members 10 can be formed by molding, for example.

1.2. Method for Separating the Separation Target

FIG. 5 is a diagram representing a method for separating the separation target using the separator 100 of FIG. 1 to FIG. 4. The present embodiment will be described through the case where cancer cells are the separation target, and the cancer cells are separated from the separation target liquid (cell suspension) using the separator 100.

When used to separate cells (for example, cancer cells) from the separation target liquid, the separator 100 according to the present embodiment can selectively separate cancer cells from the other components in the separation target liquid. As used herein, "cancer cells" means malignant tumor cells. The separation target liquid is a liquid that contains at least cells, and, potentially, cancer cells. For example, the separation target liquid is a liquid that contains cancer cells and other types of cells. Examples of the separation target liquid include bodily fluids, for example, such as blood, lymph fluid, saliva, urine, and tear, and liquids that contain these.

As illustrated in FIG. 1, in the separator 100 according to the present embodiment, the separation target liquid with a potential separation target is introduced through the inlet 30. As the separation target liquid moves within the channels 50, and the separation target (cancer cells) binds to the substance that is disposed on the side surfaces of the columnar members 10 for specific binding to the separation target (cancer cells). As a result, the cancer cells adhere to the side surfaces of the columnar members 10. The liquid from which the cancer cells have been removed then discharges through the outlet 40.

The liquid from which the cancer cells have been removed by the separator 100 according to the present embodiment can be easily collected after being discharged through the outlet 40. The separation target liquid, when it is a bodily fluid such as blood, can thus be easily returned into the body after the cancer cells are removed.

More specifically, as illustrated in FIG. 5, the separation target (cancer cells) moving near the columnar members 10 of the channels 50 is acted upon by a centripetal force 6 due to the crescent cross sections of the columnar members 10, and simultaneously by a frictional force 7 produced in reaction to the centripetal force 6. The centripetal force and the frictional force are given by the following equations.

$$\begin{aligned}\text{Centripetal Force } f1 &= (\text{volume of separation target}) \times \\ &\quad (\text{relative density of separation target}) \times \\ &\quad (\text{centrifugal acceleration}) \\ &= 1/6 * \pi * d^3 (\sigma - \rho)^* r \times \omega^2 \\ &= 1/6 * \pi * d^3 (\sigma - \rho)^* \times v^2 / r\end{aligned}$$

$$\text{Frictional Force } f2 = 3^* \pi^* d^* \eta^* v$$

In the equations, d is the diameter of the separation target, σ the density of the separation target, ρ the density of the separation target liquid, r the curvature radius of the first curve (or the second curve) of the columnar member cross section, ω the angular velocity, and η the viscosity of the separation target liquid. When σ≠ρ, the separation target in the separation target liquid moves in the deformation direction at velocity v.

Here, the relation f1=f2 is established between centripetal force f1 and frictional force f2. In this case, the sedimentation rate V of the separation target can be given by the following equation.

$$\text{Sedimentation Rate } V = d^2/18 * (\sigma - \rho)/\eta * V^2/r$$

Thus, under the conditions that the characteristics density and the viscosity of the separation target liquid moving in the channels 50 remain constant, the sedimentation rate V of the separation target is proportional to the square of the diameter d of the separation target.

Figure 10:
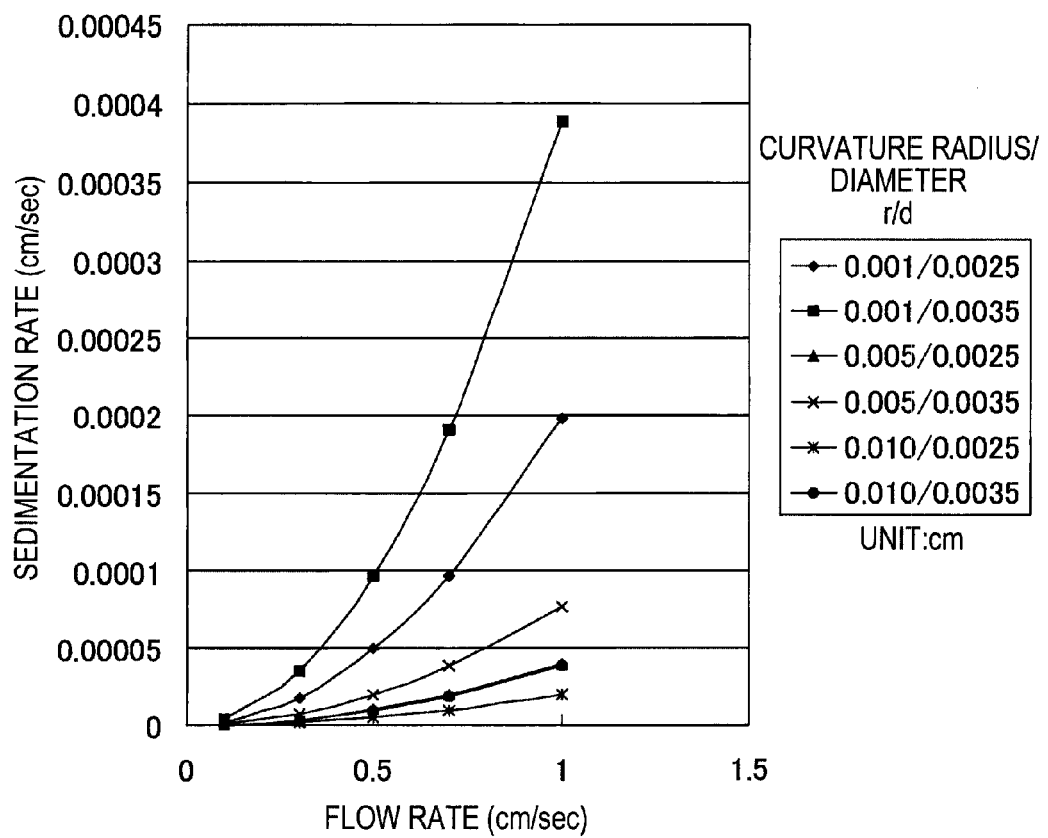
FIG. 10 is a graph representing the relationship between the flow rate of a separation target liquid and the sedimentation rate of a separation target for predetermined values of the curvature radius of the first curve of the cross section (crescent) of columnar members, and the diameter of the separation target, according to an embodiment of the present invention.

FIG. 10 is a graph representing the relationship between the flow rate of the separation target liquid and the sedimentation rate of the separation target for predetermined values of the curvature radius r of the first curve of the columnar member cross section (crescent), and the diameter d of the separation target, according to an embodiment of the invention. In the graph, the sedimentation rate of the separation target with varying diameters d of the separation target and varying curvature radiuses r of the first curve of the columnar member cross section was calculated based on the equation for sedimentation rate above, where d is the diameter (cm) of the separation target, σ the density=1.07 g/cm³ of the separation target, σ the density=1.05 g/cm³ of the separation target liquid (blood), r the first curve curvature radius (cm) of the columnar member cross section, ω the angular velocity, η the viscosity=0.035 g/cm·s of the separation target liquid (blood), and v the moving velocity=1 cm/s of the separation target (cancer cells). It can be seen from the results presented in FIG. 10 that the sedimentation rate V of the separation target decreases as the curvature radius r of the first curve of the columnar members cross section increases, and that the sedimentation rate V increases for larger diameters d of the separation target.

As illustrated in FIG. 5, the cancer cells 16a moving substantially at the middle of the space between the columnar member 10(I) and the columnar member 10(II) in direction I in the channel 50 can adhere to the side surface on the first curved surface r₁ side of the columnar member 10(I). The cancer cells 16a moving near the side surface on the second curved surface r₂ side of the columnar member 10(III) in direction II in the channel 50 can adhere to the side surface on the first curved surface r₁ side of the columnar member 10(V), even when failed to adhere to the side surface of the columnar member 10(III).

In the case of relatively smaller cancer cells 16b (cancer cells smaller than the cancer cells 16a), the cancer cells 16b moving substantially at the middle of the space between the columnar member 10(III) and the columnar member 10(IV) in direction III in the channel 50 can adhere to the side surface on the first curved surface r₁ side of the columnar member 10(VI), even when failed to adhere to the side surface on the first curved surface r₁ side of the columnar member 10(III) because of the smaller centripetal force acting on the cancer cells 16b than that on the cancer cells 16a. The cancer cells 16b moving near the side surface on the second curved surface r₂ side of the columnar member 10(IV) in direction IV in the channel 50 can adhere to the side surface on the second curved surface r₂ side of the columnar member 10(VI), even when failed to adhere to the side surface of the columnar member 10(IV).

The separator 100 according to the present embodiment is configured in such a manner that, as illustrated in FIG. 5, the plurality of columnar members 10 is arranged in row and columns. The columnar members 10 that belong to the same row (for example, columnar members 10(I) to (IV)) are disposed so that the crescents face the same direction. Further, the columnar members 10 that belong to a single row (for example, columnar members 10(I) to (IV)) are disposed so that the crescents face the opposite direction with respect to the crescents of the columnar members 10 that belong to the adjacent row (for example, columnar members 10(V) and (VI)). A substance that specifically binds to the separation target is disposed on the side surfaces 10a of the plurality of columnar members 10.

The separator 100 according to the present embodiment configured as above does not have dividing walls between the adjacent columnar members 10 in the rows (for example, between the columnar members 10(I) to (IV) and the columnar members 10(V) and (VI)). Thus, a mixing effect is produced between the separation target liquid that has passed through between the adjacent columnar members 10 in the columns (for example, between the columnar member 10(II) and the columnar member 10(III)), and the separation target liquid that has passed through between the columnar members 10 (for example, between the columnar member 10(I) and the columnar member 10(II)) adjacent to these columnar members 10. Thus, the separation target (cancer cells) has considerably greater opportunity to contact the substance disposed on the side surfaces 10a of the columnar members 10 for specific binding to the separation target. The separation target (cancer cells) can thus be efficiently trapped on the side surfaces 10a of the columnar members 10.

Again, the separator 100 according to the present embodiment includes a plurality of columnar members 100 having a crescent cross section. The columnar members 10 that belong to the same row are disposed so that the crescents face the same direction. Further, the columnar members 10 that belong to a single row are disposed so that the crescents face the opposite direction with respect to the crescents of the columnar members 10 of the adjacent row. In this way, the separation target can efficiently adhere to the side surfaces 10a of the columnar members 10 under the centripetal force due to the crescent cross section of the columnar members 100.

When cancer cells are the separation target, it is preferable that the channels 50 have a height (the height of the channels 50=the height of the columnar members 10 in the present embodiment) h of 25 µm or more, more preferably 100 µm or more, in order to enable the cancer cells to efficiently adhere to the side surfaces of the columnar members 10 without preventing their movement in the channels 50. This is because cancer cells generally have a diameter of 25 µm or more, greater than the diameters of normal cells such as white blood cells and red blood cells.

When cancer cells are the separation target, for example, antibodies that specifically bind to the cancer cells may be immobilized on the side surfaces 10a of the columnar members 10 as the substance that specifically binds to the separation target cancer cells. With such antibodies immobilized on the side surfaces 10a of the columnar members 10, the cancer cells can be captured by specific binding with the antibodies on the side surfaces 10a of the columnar members 10, and removed from the separation target liquid.

The antibodies that specifically bind to the cancer cells may be, for example, antibodies for the surface antigens of the cancer cells. When antibodies for the surface antigens of the cancer cells are used as the antibodies that specifically bind to the cancer cells, the antibodies for the surface antigens of the cancer cells can be selected according to the type of cancer cells to be separated. For example, Ep-CAM antibodies, N-cadherin antibodies, and vimentin antibodies can be used as the antibodies for the surface antigens common to carcinoma; HER2 antibodies as the antibodies for the surface antigens specific to breast cancer; NS19-9 antibodies as the antibodies for the surface antigens specific to colon cancer; and CD49, CD54, and CD59 antibodies as the antibodies for the surface antigens specific to prostate cancer. These are examples of antibodies that can be immobilized.

Further, an apoptosis-inducing factor may be immobilized on the side surfaces 10a of the columnar members 10 as the substance that specifically binds to the separation target cancer cells. With the apoptosis-inducing factor immobilized on the side surfaces 10a of the columnar members 10, the cancer cells can be induced to necrosis upon contact with the apoptosis-inducing factor on the side surfaces 10a of the columnar members 10.

Any apoptosis-inducing factor can be used, as long as it can induce apoptosis of cancer cells. Examples include TNF-α, TNF-γ, TRAIL, Fas, lymphotoxin, acyclic retinoid, bikunin, parasporin, mitomycin, taxol, and adiponectin.

The antibodies or apoptosis-inducing factor can be immobilized on the side surfaces 10a of the columnar members 10 using physical adsorption methods or chemical binding methods. Chemical binding methods are advantageous in terms of ensuring immobilization. For example, when the surfaces are material that includes hydroxyl groups, the antibodies can be immobilized on the surfaces by chemical binding in a reaction between the hydroxyl groups and the active ester groups activated beforehand by the esterification of the antibody carboxyl groups.

The side surfaces 10a of the columnar members 10 may be a silicon oxide film. When a silicon oxide film is used, the side surfaces 10a of the columnar members 10 become hydrophilic, and thus provide good affinity to the antibodies or apoptosis-inducing factor that specifically bind to the cancer cells. Further, the hydroxyl groups contained in the silicon oxide film can be used to attach the antibodies or apoptosis-inducing factor on the surfaces.

When cancer cells are the separation target, the cancer cells to be separated may be, for example, circulating tumor cells (CTCs). When the bodily fluid is blood or a lymph fluid, the blood or lymph fluid can be returned to the patient's body after the CTCs are removed from the collected blood or lymph fluid of the patient, using the separator 100 according to the present embodiment. In this way, cancer metastasis can be suppressed in the patient. For example, by selectively separating CTCs from blood, the CTCs can be separated from the other components (for example, normal cells such as red blood cells, white blood cells, and platelets; salts; plasma proteins such as albumin; antibodies such as immunoglobulins; and blood coagulation factors), with minimum damage to these components. The bodily fluid may be diluted.

The removal of CTCs using the separator 100 according to the present embodiment may accompany radiation therapy and/or chemotherapy, or may be used instead of radiation therapy or chemotherapy. Specifically, a cancer therapeutic method and/or a cancer prevention method according to an embodiment of the present invention includes removing cancer cells from a bodily fluid collected from a patient, and returning the bodily fluid into the body of the patient, using the separator 100 of the present embodiment. The bodily fluid can be returned to the patient's body using, for example, techniques used for blood dialysis.

The separation target was described as being cancer cells in the present embodiment. However, the separation target of the separator 100 according to the present embodiment may be, for example, non-cancer cells, viruses, bacteria, proteins, low- to high-molecular compounds, particles, colloids, allergic substances, for example, such as pollen, toxic substances, harmful substances, and environmental pollutants. The separator 100 according to the present embodiment also can be used as a device for blood dialysis, blood purification, induction of cell differentiation, and gene introduction.

1.3. Variations

Figure 6:
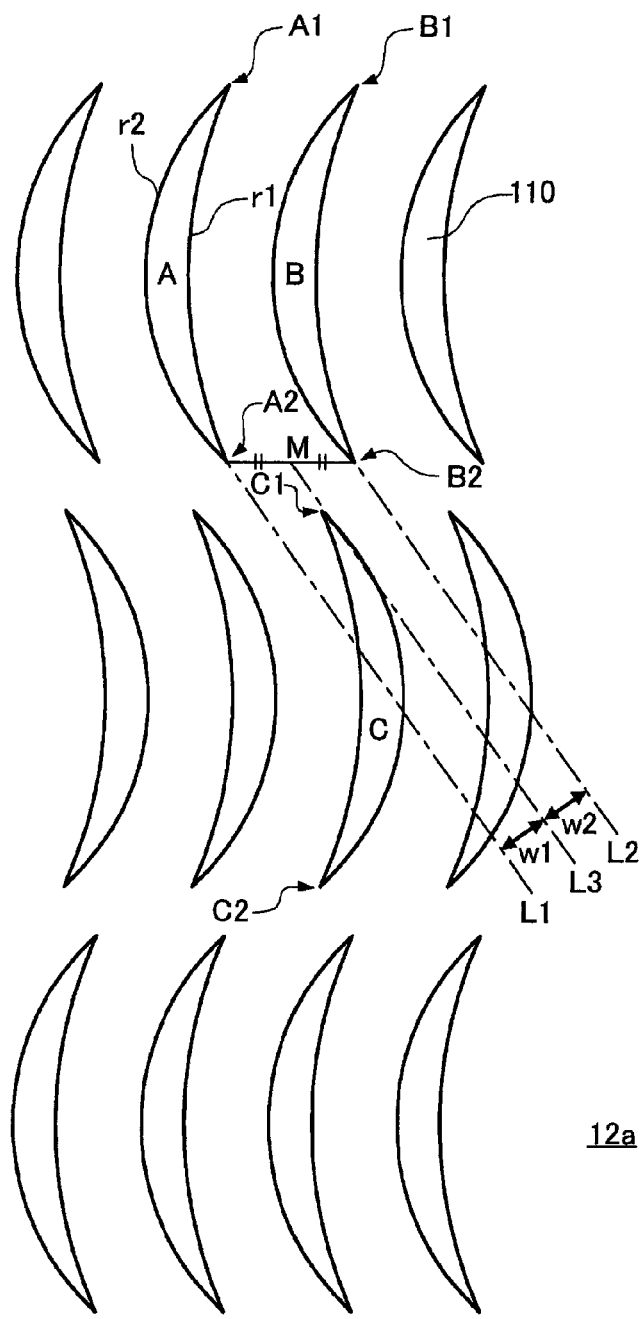
FIG. 6 is a diagram illustrating a variation of the plane pattern of the plurality of columnar members shown in FIG. 2.
Figure 7:
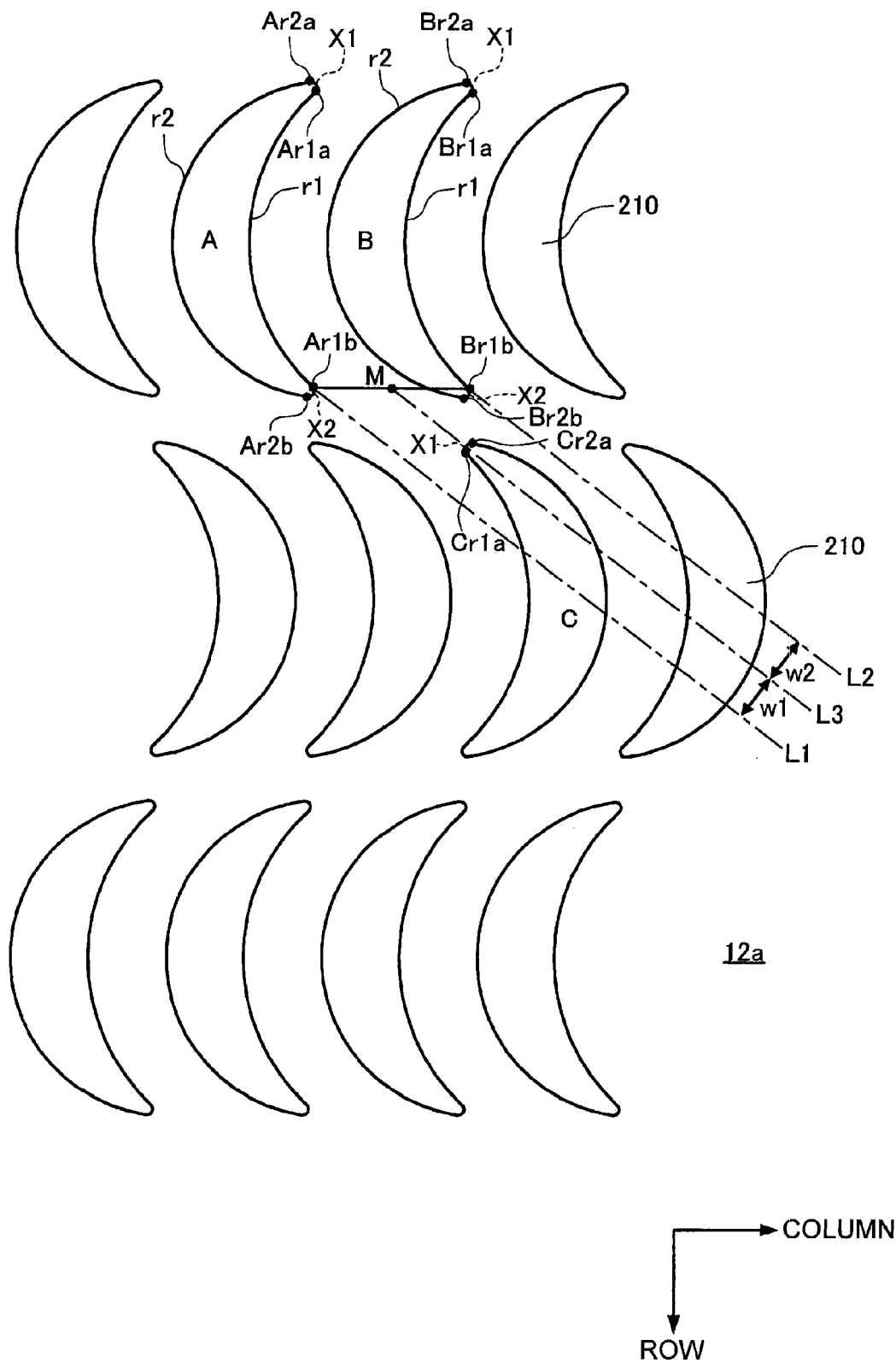
FIG. 7 is a diagram illustrating another variation of the plane pattern of the plurality of columnar members shown in FIG. 2.
Figure 8:
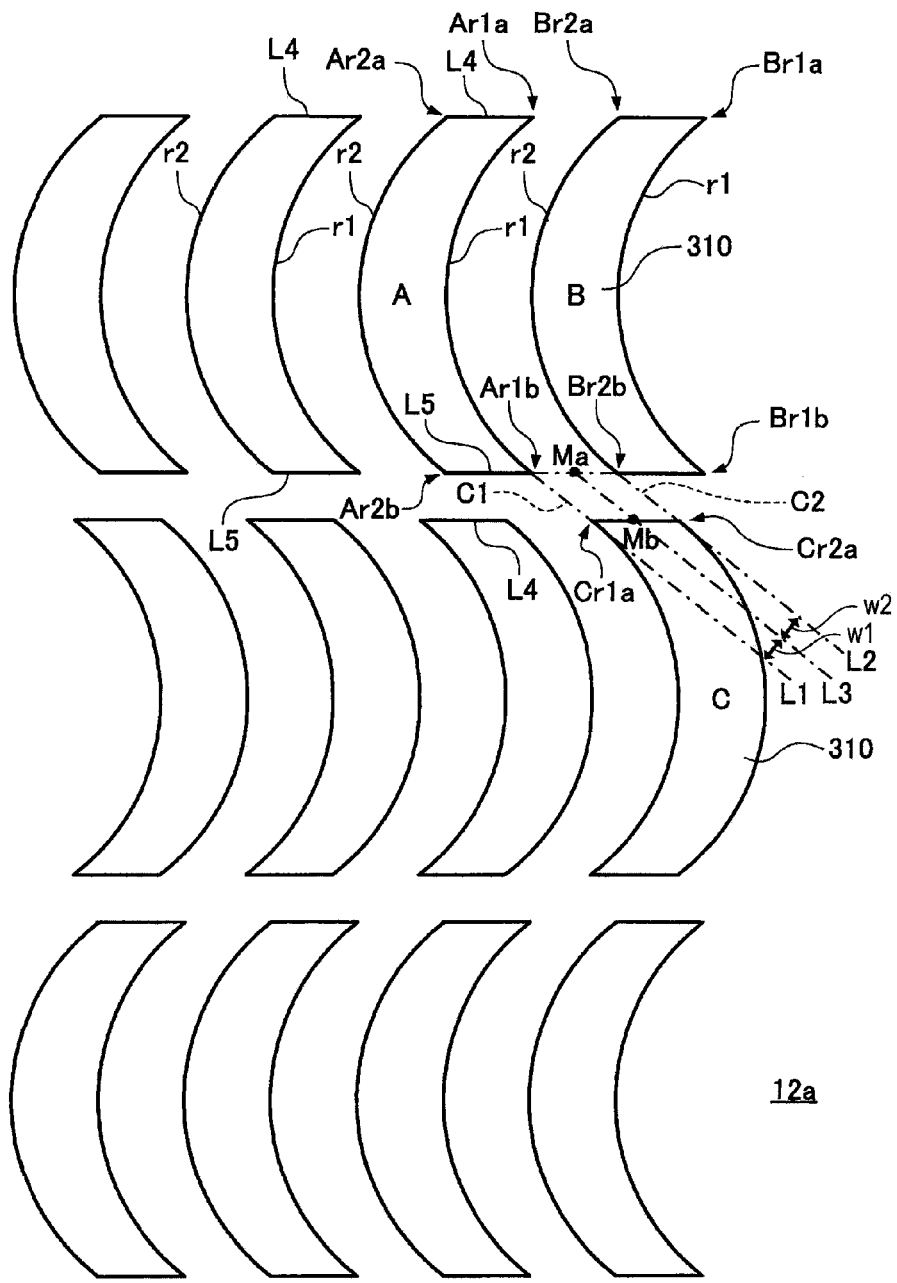
FIG. 8 is a diagram illustrating yet another variation of the plane pattern of the plurality of columnar members shown in FIG. 2.

FIG. 6 is a diagram illustrating a variation (Variation 1) of the plane pattern of the plurality of columnar members 10 shown in FIG. 2. FIG. 7 is a diagram illustrating another variation (Variation 2) of the plane pattern of the plurality of columnar members 10 shown in FIG. 2. FIG. 8 is a diagram illustrating yet another variation (Variation 3) of the plane pattern of the plurality of columnar members 10 shown in FIG. 2. In the following variations, the same reference numerals are used for the same components described in First Embodiment, and explanations thereof are omitted.

1.3.1. Variation 1

In the columnar members 110 illustrated in FIG. 6, the first curve $r_1$ and the second curve $r_2$ defining the crescent cross section have smaller curvatures than their counterparts in the columnar members 10 of FIG. 2. The curvatures of the first curve $r_1$ and the second curve $r_2$ can be appropriately determined according to such conditions as, for example, the diameter of the separation target, the flow rate and viscosity of the separation target liquid, the size of the channels, and the distance between adjacent columnar members. The centripetal force that acts on the separation target can be adjusted by adjusting the curvatures of the first curve $r_1$ and the second curve $r_2$.

1.3.2. Variation 2

The columnar members 210 illustrated in FIG. 7 differ from the columnar members 10 shown in FIG. 2 in that one end portion $r_{1a}$ of the first curve $r_1$ and one end portion $r_{2a}$ of the second curve $r_2$ in the crescent cross section are connected to each other with a curve $X_1$, and that the other end portion $r_{1b}$ of the first curve $r_1$ and the other end portion $r_{2b}$ of the second curve $r_2$ are connected to each other with a curve $X_2$.

In FIG. 7, M is the center of the line that links the second end portion $Ar_{1b}$ of the first curve $r_1$ of a columnar member 210A, and the second end portion $Br_{1b}$ of the first curve $r_1$ of a columnar member 210B adjacent to the columnar member 210A in the column direction, $L_1$ is the straight line that extends from the second end portion $Ar_{1b}$ of the first curve $r_1$ of the columnar member 210A along the tangent line direction, $L_2$ is the straight line that extends from the second end portion $Br_{1b}$, of the first curve $r_1$ of the columnar member 210B along the tangent line direction, and $L_3$ is the line that passes the apex of the curve $X_1$ of the columnar member 210C closest to the center M aside from the columnar member 210A and the columnar member 210B, and is parallel to the straight line $L_1$ and the straight line $L_2$. It is preferable that the straight line $L_3$ lie between the straight line $L_1$ and the straight line $L_2$. As used herein, the "apex" of the curve $X_1$ of the columnar member 210C is the point at the peak of the curve $X_1$ with respect to the direction along the straight line $L_1$ or $L_2$.

In Variation 2 of FIG. 7, it is preferable that the distance $w_1$ between the straight line $L_1$ and the straight line $L_3$, and the distance $w_2$ between the straight line $L_2$ and the straight line $L_3$ be related to each other at the ratio $w_1/w_2$ of 0.8 to 1.2, so that the separation target that has passed through between the columnar member 210A and the columnar member 210B has the greater chance to adhere to the side surfaces of the columnar member 210C. In FIG. 7, $w_1/w_2 = 1.0$ (the straight line $L_3$ lies on center M).

1.3.3. Variation 3

The columnar members 310 illustrated in FIG. 8 differ from the columnar members 10 of FIG. 2 in that one end portion $r_{1a}$ of the first curve $r_1$ and one end portion $r_{2a}$ of the second curve $r_2$ in the crescent cross section are connected to each other with a straight line $L_4$, and that the other end portion $r_{1b}$ of the first curve $r_1$ is connected to the other end portion $r_{2b}$ of the second curve $r_2$ with a straight line $L_5$.

In FIG. 8, $M_a$ is the center of the line that links the second end portion $Ar_{1b}$, of the first curve $r_1$ of a columnar member 310A, and the second end portion $Br_{2b}$ of the second curve $r_2$ of a columnar member 310B adjacent to the columnar member 310A in the column direction, $L_1$ is the straight line that extends from the second end portion $Ar_{1b}$, of the first curve $r_1$ of the columnar member 310A along the tangent line direction, $L_2$ is the straight line that extends from the second end portion $Br_{2b}$ of the second curve $r_2$ of the columnar member 310B along the tangent line direction, and $L_3$ is the line that passes the center $M_b$ of the straight line $L_4$ of a columnar member 310C closest to the center $M_a$ aside from the columnar member 310A and the columnar member 310B, and is parallel to the straight line $L_1$ and the straight line $L_2$. It is preferable that the straight line $L_3$ lie between the straight line $L_1$ and the straight line $L_2$.

In Variation 3 of FIG. 8, it is preferable that the distance $w_1$ between the straight line $L_1$ and the straight line $L_3$, and the distance $w_2$ between the straight line $L_2$ and the straight line $L_3$ be related to each other at the ratio $w_1/w_2$ of 0.8 to 1.2, so that the separation target that has passed through between the columnar member 310A and the columnar member 310B has the greater chance to adhere to the side surfaces of the columnar member 310C. In FIG. 8, $w_1/w_2 = 1.0$ (the straight line $L_3$ lies on center $M_a$).

In Variation 3 of FIG. 8, one end portion $r_{1a}$ of the first curve $r_1$ and one end portion $r_{2a}$ of the second curve $r_2$ of the columnar member 310, and/or the other end portion $r_{1b}$ of the first curve $r_1$ and the other end portion $r_{2b}$ of the second curve $r_2$ of the columnar member 310 may be connected to each other via a curve, as in Variation 2 of FIG. 7.

2. Second Embodiment

Figure 9:
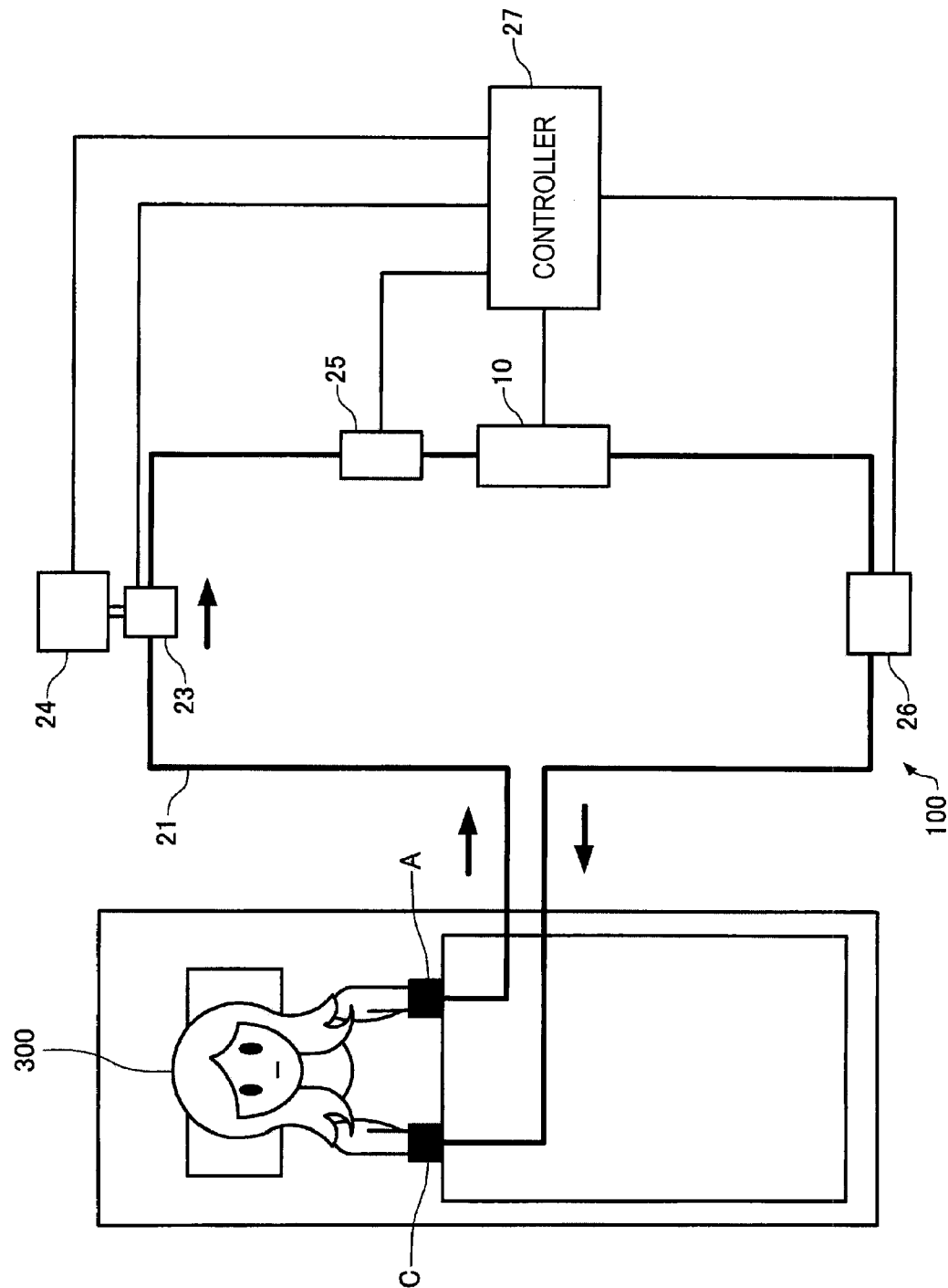
FIG. 9 is an explanatory diagram representing a separator system according to Second Embodiment of the present invention.

FIG. 9 is a diagram schematically illustrating a separator system (cancer cell removing system) 1000 according to an embodiment of the present invention. The present embodiment will be described through the case where the separator system 1000 is used to remove cancer cells. However, as noted in First Embodiment, the separator system 1000 according to the present embodiment can be used to separate separation targets other than cancer cells.

As illustrated in FIG. 9, the separator system 1000 according to the present embodiment includes the separator 100 of First Embodiment, and a controller 27. The separator 100 removes cancer cells from the bodily fluid collected from a patient 300. The separator system 1000 further includes a tube 21 used for the transfer of the bodily fluid collected from the patient 300, a pump 23 that drives the transfer of the bodily fluid through the tube 21, and pressure monitoring units 25 and 26 that monitor the pressure of the bodily fluid in the tube 21. The separator 100, the pump 23, and the pressure monitoring units 25 and 26 are connected to each other via the tube 21. The separator system 1000, described as being provided with a single separator 100 in this embodiment, may include more than one separator 100.

As illustrated in FIG. 9, the two terminals A and C of the tube 21 are attached to the patient 300, and the bodily fluid is collected from the patient 300 under the driving of the pump 23. The bodily fluid is then introduced into the separator 100 through the terminal (collecting end) A via the tube 21, and the separator 100 removes the cancer cells from the bodily fluid. After the removal of the cancer cells, the bodily fluid is returned into the body of the patient 300 through the terminal (receiving end) C via the tube 21 under the driving of the pump 23. For example, the separator system 1000 according to the present embodiment can be used to collect a bodily fluid from the body of the patient 300, and to return the processed bodily fluid into the body of the patient 300, using techniques used for blood dialysis. When the bodily fluid is blood, an anticoagulant may be introduced into the tube 21 from an anticoagulant supply unit 24, in order to prevent coagulation of the blood in the tube 21.

In the separator system 1000 according to the present embodiment, the controller 27 is electrically or optically connected to the separator 100, the pressure monitoring units 25 and 26, the pump 23, and the anticoagulant supply unit 24, as illustrated in FIG. 9. The controller 27 is adapted to receive information from the electrically or optically connected components in the form of electrical or light signals, and send information to these components in the form of electrical or light signals. The controller 27 can be executed, for example, by means of software installed in a computer.

The separator 100 may be used for extracorporeal circulation as illustrated in FIG. 9, or may be embedded in the body of the patient 300. Further, the separator 100 may be included in a separator cartridge. The pump 23 and the pressure monitoring units 25 and 26 may be those used for blood dialysis, for example.

The separator system 1000 according to the present embodiment uses the separator 100 to remove the separation target (cancer cells) from the bodily fluid collected from the patient 300, and returns the bodily fluid into the body of the patient 300. When provided as a separator cartridge, the separator 100 can be easily replaced by detaching the separator cartridge after use.

The invention has been described with respect to certain embodiments. The invention encompasses configurations essentially the same as those described in the embodiments (for example, a configuration with the same functions, methods, and results, and a configuration with the same object and results). The invention also encompasses configurations that have replaced non-essential components of the configurations described in the embodiments. The invention also encompasses configurations that have the same effects or achieve the same object as the configurations described in the embodiments. The invention also encompasses configurations that include the configurations of the foregoing embodiments in combination with the related art.

What is claimed is:

1. A separator comprising:
a channel having a first surface;
a plurality of columnar members formed on the first surface and having a cross section in the shape of a crescent,
the plurality of columnar members being arranged in a row direction along a longitudinal direction of the channel, and in a column direction perpendicular to the longitudinal direction of the channel,
the columnar members that belong to the same row from among the plurality of columnar members being disposed so that the crescents face the same direction in the column direction,
the columnar members that belong to a single row being disposed so that the crescents face the opposite direction in the column direction with respect to the crescents of the columnar members that belong to the adjacent row; and
a substance that specifically binds to a separation target, and is disposed on side surfaces of the plurality of columnar members.

2. The separator according to claim 1,
wherein the crescent includes a first curve, and a second curve having a greater curvature than the first curve,
the first curve having an end portion in contact with one end portion of the second curve at a first end portion,
the other end portion of the first curve being in contact with the other end portion of the second curve at a second end portion, and
wherein a straight line $L_3$ lies between a straight line $L_1$ and a straight line $L_2$ under the conditions that:
$A_2$ is the second end portion of a columnar member A,
$B_2$ is the second end portion of a columnar member B adjacent to the columnar member A in the column direction,
$L_1$ is a straight line that extends from the second end portion $A_2$ of the columnar member A along a direction of a tangent line to the first curve at the second end portion $A_2$,
$L_2$ is a straight line that extends from the second end portion $B_2$ of the columnar member B along a direction of a tangent line to the first curve at the second end portion $B_2$,
M is the center of a segment that links the second end portion $A_2$ and the second end portion $B_2$,
$C_1$ is the first end portion of a columnar member C adjacent to the columnar member A and the columnar members B in the row direction, and closest to the center M aside from the columnar member A and the columnar member B, and
$L_3$ is a straight line that passes the first end portion $C_1$, and is parallel to the straight line $L_1$ and the straight line $L_2$.

3. The separator according to claim 2, wherein a distance $w_1$ between the straight line $L_1$ and the straight line $L_3$, and a distance $w_2$ between the straight line $L_2$ and the straight line $L_3$ are related to each other at the ratio $w_1/w_2$ of 0.8 to 1.2.

4. A separator cartridge comprising the separator of claim 1.

5. A separator for separating a separation target from a separation target liquid,
the separator comprising a channel through which the separation target liquid is flown,
wherein the channel includes:
a first columnar member having a cross section in the shape of a crescent, and side surfaces on which a substance that specifically binds to the separation target is disposed;
a second columnar member having a cross section in the shape of a crescent, and that belongs to the same position as the first columnar member with respect to a first direction along a longitudinal direction of the channel, and to a position adjacent to the first columnar member with respect to a second direction orthogonal to the first direction, wherein the crescent of the second columnar member faces the same direction as the crescent of the first columnar member in the second direction, and wherein the substance is disposed on side surfaces of the second columnar member; and
a third columnar member having a cross section in the shape of a crescent, and that belongs to a position adjacent to the first columnar member with respect to the first direction, wherein the crescent of the third columnar member faces the opposite direction in the second direction with respect to the crescent of the first columnar member, and wherein the substance is disposed on side surfaces of the third columnar member.

6. The separator according to claim 5,
wherein the crescent includes a first curve, and a second curve having a greater curvature than the first curve,
the first curve having an end portion in contact with one end portion of the second curve at a first end portion,
the other end portion of the first curve being in contact with the other end portion of the second curve at a second end portion, and
wherein a straight line $L_3$ lies between a straight line $L_1$ and a straight line $L_2$ under the conditions that:
$A_2$ is the second end portion of the first columnar member,
$B_2$ is the second end portion of the second columnar member,
$L_1$ is a straight line that extends from the second end portion $A_2$ along a direction of a tangent line to the first curve of the first columnar member at the second end portion $A_2$, $L_2$ is a straight line that extends from the second end portion $B_2$ along a direction of a tangent line to the first curve of the second columnar member at the second end portion $B_2$, M is the center of a segment that links the second end portion $A_2$ and the second end portion $B_2$, $C_1$ is the first end portion of the third columnar member, and $L_3$ is a straight line that passes the first end portion $C_1$, and is parallel to the straight line $L_1$ and the straight line $L_2$.

7. The separator according to claim 6, wherein a distance $w_1$ between the straight line $L_1$ and the straight line $L_3$, and a distance $w_2$ between the straight line $L_2$ and the straight line $L_3$ are related to each other at the ratio $w_1/w_2$ of 0.8 to 1.2.

* * * * *